(12) United States Patent
Bidlingmeyer et al.

(10) Patent No.: US 7,112,277 B2
(45) Date of Patent: Sep. 26, 2006

(54) METHODS AND SYSTEMS FOR SEPARATING CONSTITUENTS OF A HIGHLY AQUEOUS FLUID

(75) Inventors: Brian A. Bidlingmeyer, Frazer, PA (US); Alan D. Broske, West Chester, PA (US)

(73) Assignee: Agilent Technologis, Inc., Palo Alto, CA (US)

( * ) Notice: Subject to any disclaimer, the term of this patent is extended or adjusted under 35 U.S.C. 154(b) by 130 days.

(21) Appl. No.: 10/611,171

(22) Filed: Jun. 30, 2003

(65) Prior Publication Data

US 2004/0262224 A1    Dec. 30, 2004

(51) Int. Cl.
B01D 15/08    (2006.01)

(52) U.S. Cl. ............... 210/198.2; 210/502.1; 210/635; 210/656

(58) Field of Classification Search ........ 210/635, 210/656, 198.2, 502.1
See application file for complete search history.

(56) References Cited

U.S. PATENT DOCUMENTS

| | | | | |
|---|---|---|---|---|
| 4,919,804 A * | 4/1990 | Dorsey et al. | ......... | 210/198.2 |
| 5,277,813 A * | 1/1994 | Feibush et al. | ......... | 210/502.1 |
| 5,374,755 A * | 12/1994 | Neue et al. | ......... | 556/400 |
| 5,667,674 A * | 9/1997 | Hanggi et al. | ......... | 210/198.2 |
| 5,876,595 A * | 3/1999 | Hanggi et al. | ......... | 210/198.2 |
| 6,277,782 B1 * | 8/2001 | Moller et al. | ......... | 502/402 |
| 6,365,105 B1 * | 4/2002 | Waters et al. | ......... | 422/70 |
| 6,503,397 B1 * | 1/2003 | Gjerde et al. | ......... | 210/635 |

OTHER PUBLICATIONS

Snyder (Introduction to Modern Liquid Chromatography,John Wiley, New York, 1979, pp. 493-494).*
Snyder, Introduction to Modern Liquid Chromatography, John Wiley, New York 1979, p. 275.*
Snyder, Introduction to Modern Liquid Chromatography, John Wiley, New York 1979, p. 182.*
John E. O'Gara etal., entitled "Embedded-Polar-Group Bonded Phases for High Performance Liquid Chromatography," LCGC, vol. 19, No. 6, Jun. 2001, pp. 632-642.
Ronald E. Majors et al., entitled "Column for Reversed-Phase LC Separations in Highly Aqueous Mobile Phases," LCGC North America, vol. 20, No. 7, Jul. 2002, pp. 584-593.
Matthew Przybyciel et al., entitled "Phase Collapse in Reversed-Phase LC," Column Watching, LCGC Europe, Oct. 2002, pp. 2-5.
Terrence S. Reid et al, entitled "Compatibility of C18 HPLC Columns with Pure Aqueous Mobile Phase," American Labiratory, Jul. 1999, pp. 24-28.

* cited by examiner

Primary Examiner—Ernest G. Therkorn
(74) Attorney, Agent, or Firm—Agilent Technologies, Inc.

(57) ABSTRACT

The subject invention includes methods and devices for separating at least two constituents of a highly aqueous fluid. The subject methods include contacting a highly aqueous fluid with a stationary phase having a low density hydrophobic bonded phase under conditions to separate at least two constituents. Also provided are systems that include a stationary phase having a low density hydrophobic bonded phase, a highly aqueous fluid comprising at least two constituents and a device configured to perform liquid chromatography. Kits for use in practicing the subject methods are also provided.

22 Claims, 2 Drawing Sheets

| | Nicotonic Acid | | | Pyridoxine | | | Thiamine | | | Niacinamide | | |
|---|---|---|---|---|---|---|---|---|---|---|---|---|
| | K' Before | K' After | %Difference | K' Before | K' After | % Difference | K' Before | K' After | % Difference | K' Before | K' After | % Difference |
| C1 C18 80A | 1.25 | 0 | 0 | 5.29 | 0.37 | 6.99 | 6.86 | 0.54 | 7.87 | 6.86 | 0.54 | 7.87 |
| C2 C18 300A | 0.98 | 0.97 | 98.98 | 3.17 | 3.12 | 98.42 | 5.67 | 5.4 | 95.24 | 3.96 | 3.9 | 98.48 |
| C3 C18 800A | 0.371 | 0.374 | 100.81 | 0.996 | 1.01 | 101.41 | 1.247 | 1.263 | 101.28 | 1.247 | 1.263 | 101.28 |
| B1 C18 80A | 1.66 | 0.28 | 16.87 | 7.16 | 1.48 | 20.67 | 9.6 | 2 | 20.83 | 8.52 | 1.84 | 21.60 |
| B2 C18 150A | 1.42 | 1.28 | 90.14 | 5.62 | 5.06 | 90.04 | 6.87 | 6.22 | 90.54 | 7.8 | 6.96 | 89.23 |
| B3 C18 150A | 1.41 | 1.28 | 90.78 | 5.59 | 5 | 89.45 | 6.83 | 6.14 | 89.90 | 7.78 | 6.91 | 88.82 |
| B4 C18 300A | 1.81 | 1.83 | 101.10 | 5.2 | 5.25 | 100.96 | 6.34 | 6.36 | 100.32 | 6.34 | 6.36 | 100.32 |
| A1 C18 80A | 0.9 | 0.91 | 101.11 | 2.03 | 2.05 | 100.99 | 2.57 | 2.56 | 99.61 | 2.39 | 2.42 | 101.26 |
| A2 C18 100A | 2.74 | 1.91 | 69.71 | 9.32 | 6.09 | 65.34 | 13.48 | 8.66 | 64.24 | 17.06 | 12.4 | 72.68 |
| A3 C18 150A | 1.9 | 1.84 | 96.84 | 6.712 | 6.54 | 97.44 | 12.2 | 11.91 | 97.62 | 12.2 | 11.91 | 97.62 |
| A4 C18 300A | 1.43 | 1.43 | 100.00 | 5.13 | 5.12 | 99.81 | 7.41 | 7.41 | 100.00 | 7.41 | 7.41 | 100.00 |
| D1 C8 80A | 1.17 | 1.18 | 100.85 | 3.36 | 3.37 | 100.30 | 4.76 | 4.74 | 99.58 | 5.36 | 5.38 | 100.37 |
| D2 C8 300A | 3.3 | 3.18 | 96.36 | 7.68 | 7.28 | 94.79 | 17.74 | 16.57 | 93.40 | 20.25 | 19.65 | 97.04 |
| E CN 80A | 1.44 | 1.44 | 100.00 | 2.66 | 2.64 | 99.25 | 6.1 | 6.09 | 99.84 | 6.1 | 6.09 | 99.84 |
| G NH₂ 70A | 1.57 | 1.58 | 100.64 | 2 | 2 | 100.00 | 4.96 | 4.94 | 99.60 | 5.66 | 5.64 | 99.65 |
| | 7.68 | 7.64 | 99.48 | 0.45 | 0.45 | 100.00 | 0.16 | 0.16 | 100.00 | 0.91 | 0.9 | 98.90 |
| F Phenyl 80A | Only two peaks observed, % difference for the two peaks was 99.3% | | | | | | | | | | | |
| Micra NPS RP-18 | 0.55 | 0.54 | 98.1818182 | 0.85 | 0.85 | 100 | 1.25 | 1.24 | 99.2 | 0.85 | 0.85 | 100 |

FIG. 2

METHODS AND SYSTEMS FOR SEPARATING CONSTITUENTS OF A HIGHLY AQUEOUS FLUID

FIELD OF THE INVENTION

The field of this invention is chromatography, and more specifically liquid chromatography such as high performance liquid chromatography.

BACKGROUND OF THE INVENTION

The goal of many chemical analysis protocols is to separate a sample (blood, tears, urine, water from a well, etc.) into its individual components or constituents so that each component may be evaluated without any interference from other components. One technique that is often employed to separate various constituents of a sample from each other is chromatography, where liquid chromatography ("LC") is often employed. Liquid chromatography is an analytical chromatographic technique that is useful for separating ions or molecules that are dissolved in a liquid or solvent. If the sample solution is in contact with a second solid or liquid phase, the different solutes will interact with the other phase to differing degrees due to differences in adsorption, ion-exchange, partitioning, or size. These differences allow the mixture components to be separated from each other by using these differences to determine the transit time of the solutes through a column. Chromatography may be coupled with a suitable detection system that can characterize each type of separated constituent. One liquid chromatography protocol that is often employed due to its versatility is high performance liquid chromatography ("HPLC").

Generally, HPLC includes passing a sample of constituents in a high pressure fluid or solvent (called the mobile phase) through a tube or column. The column is packed with a stationary phase. The stationary phase is typically composed of a substrate such as particles, e.g., porous beads or the like. The pore sizes can be varied to allow certain sized analytes to pass through at different rates. As the constituents pass through the column they interact with the mobile and stationary phases at different rates. The difference in rates is due to the difference in one or more physical properties of the constituents, e.g., different polarities. The constituents that have the least amount of interaction with the stationary phase, or the most amount of interaction with the mobile phase, will thus exit the column faster.

As the various constituents exit the column, they can be detected by various techniques, e.g., refractive index, electrochemical, or ultraviolet-absorbance, which can indicate the presence of a constituent. The amount of constituent exiting the column may be determined by the intensity of the signal produced in a detector. A detector is employed to measure a signal peak as each constituent exits the column. By comparing the time it takes for the peak to show up (also referred to as the retention time) with the retention times for a mixture of known compounds, the constituents of unknown sample mixtures can be identified. By measuring the signal intensity (also referred to as the response) and comparing it to the response of a known amount of that particular analyte, the amount of analyte in the mixture can be determined.

One particularly useful mode of HPLC—particularly for the separation of highly polar or ionizable constituents, is reversed phase high performance liquid chromatography ("RP-HPLC"). RP-HPLC primarily operates on the basis of hydrophilicity and lipophilicity to separate various constituents of a liquid medium from each other. The stationary phase includes a substrate (which may be a plurality of particles) that has bound chemical moieties (i.e., a bonded phase), such as hydrophobic chains, e.g., bound alkyl chains, and the like, which facilitate the separation of the constituents. Accordingly, the greater the hydrophobicity of the bound chemical moieties, the greater is the tendency of the hydrophobic constituents in the mobile phase to be retained in the column while the hydrophilic constituents are eluted more rapidly from the column than the hydrophobic constituents.

Regardless of the type of liquid chromatography protocol employed, the particular mobile phase employed is important to the outcome of the protocol. For example, in order to achieve sufficient retention of certain constituents, it may be necessary to use a high aqueous mobile phase. However, when such high aqueous mobile phases are used, it is not uncommon to observe a decrease in retention of constituents over the course of the chromatography procedure, where oftentimes retention times are decreased to a point that any separation of constituents is lost.

While it is not completely clear why this loss in retention occurs when employing a high aqueous mobile phase with a stationary phase that includes hydrophobic functional groups—as is the case with RP-HPLC, it is hypothesized that the hydrophobic bonded phase (e.g., bonded alkyl chains) that is fully extended or solvated in an organic phase (e.g., 100% methanol) collapses in the highly aqueous mobile phase employed in the chromatography protocol. In other words, this behavior of retention decreasing over time in a high aqueous mobile phase is thought to be attributed to the chains of the functional groups of the stationary phase "collapsing" onto other chains and onto the surface of the particles to which they are bonded. Accordingly, this phenomenon is often referred to as "phase collapse". When phase collapse occurs, the surface of the stationary phase is less accessible as compared to a surface where the chains are fully extended. Accordingly, when phase collapse occurs, there is less availability of the bonded phase to interact with sample constituents and consequently retention decreases.

A variety of techniques have been developed to try to combat phase collapse. One such technique that is often employed reverses the phase collapse process. This is accomplished by flooding the stationary phase with significant volumes of a high organic content mobile phase followed by quickly switching back to the high aqueous phase. However, this is not a complete solution as the retention will again decrease when the highly aqueous mobile phase is used. Another technique is to incorporate polar groups near the substrate surface which interact with the highly aqueous phase and provide a solvated surface that helps prevent phase collapse. However, this technique also has disadvantages, as retention times are typically much lower than protocols without these polar groups and the protocols for fabricating such stationary phases increases in complexity, thus increasing manufacturing costs.

Accordingly, there continues to be an interest in the development of new methods and devices for separating constituents of a highly aqueous fluid. Of particular interest is the development of such methods and devices that do not exhibit phase collapse, are easy to use and are cost effective.

REFERENCES OF INTEREST INCLUDE: J. E. O'Gara, et al., Embedded Polar Group Bonded Phases for High Performance Liquid Chromatography, *LCGC,* 19(6), 632 (2001); Reid, et al., Compatibility of C18 HPLC Columns with Pure Aqueous Mobile Phase, *American Lab.*, 7, 24 (1999); Przybyciel, et al., Phase Collapse in Reversed-Phase LC, *LCGC*, 20(6), 516 (2002).

SUMMARY OF THE INVENTION

The subject invention includes methods and devices for separating at least two constituents of a highly aqueous fluid. The subject methods include contacting a highly aqueous fluid with a stationary phase having a low density hydrophobic bonded phase under conditions to separate at least two constituents. Also provided are systems that include a stationary phase having a low density hydrophobic bonded phase, a highly aqueous fluid comprising at least two constituents and a device configured to perform liquid chromatography. Kits for use in practicing the subject methods are also provided.

BRIEF DESCRIPTIONS OF THE DRAWINGS

FIG. 2 shows the results of employing the subject invention with various phases to separate various water-soluble B vitamins.

DETAILED DESCRIPTION OF THE INVENTION

Figure 1:
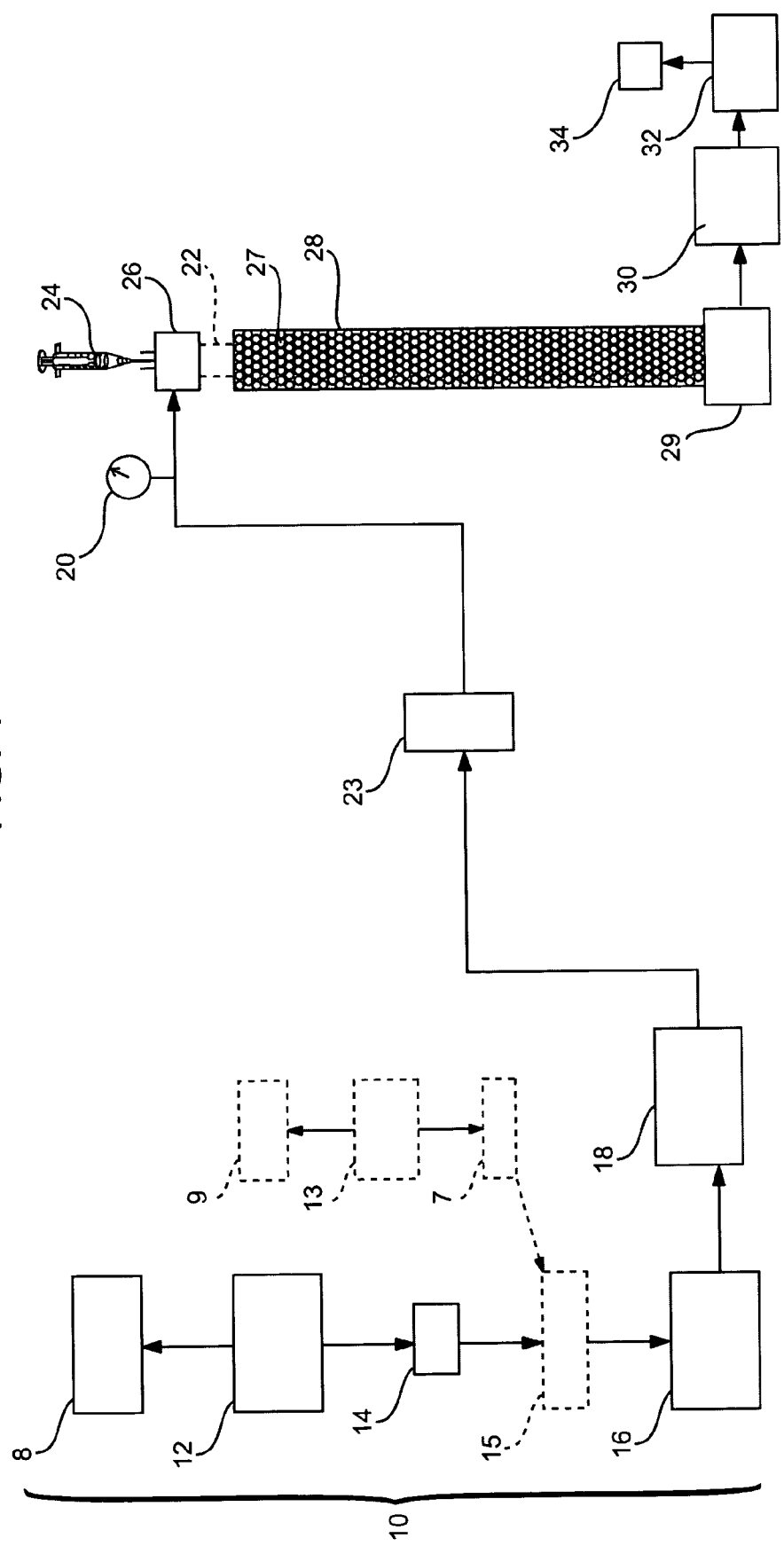
FIG. 1 shows an exemplary embodiment of a subject system for separating at least two constituents of a highly aqueous fluid.

The subject invention includes methods and devices for separating at least two constituents of a highly aqueous fluid. The subject methods include contacting a highly aqueous fluid with a stationary phase having a low density hydrophobic bonded phase under conditions to separate at least two constituents. Also provided are systems that include a stationary phase having a low density hydrophobic bonded phase, a highly aqueous fluid comprising at least two constituents and a device configured to perform liquid chromatography. Kits for use in practicing the subject methods are also provided.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

In further describing the subject invention, the subject methods are first described in greater detail, followed by a description of systems and kits for use in practicing the subject methods.

Methods

As summarized above, the subject invention includes methods for separating at least two constituents of a highly aqueous fluid. In general, in accordance with the subject methods a highly aqueous fluid is provided that includes at least two constituents. The highly aqueous fluid is then contacted with a stationary phase under conditions sufficient to separate the at least two constituents. In many embodiments, the subject methods are methods of performing liquid chromatography ("LC"), and in many embodiments the subject methods are methods of performing high performance liquid chromatography ("HPLC"), where in certain embodiments the subject methods are methods for performing reversed phase high performance liquid chromatography ("RP-HPLC"). In accordance with the subject invention, the stationary phase of the subject invention is made up of a substrate, e.g., a plurality of particles, and a hydrophobic phase bonded to the substrate. A feature of the subject methods is that the bonding density of the hydrophobic bonded phase is low such that the hydrophobic bonded phase may be characterized as low density hydrophobic bonding density. In other words, the denseness of the bonding of the hydrophobic bonded phase per unit area to the substrate is low.

The subject methods provide for unexpected results as realized by the inventors of the subject invention. Specifically, when employing a stationary phase having a low density hydrophobic bonded phase with a highly aqueous fluid to separate constituents of the highly aqueous fluid, phase collapse as described above is significantly reduced and in many embodiments is completely eliminated. This beneficial result is unexpected in that there is no indication in the prior art that contacting a highly aqueous fluid with a stationary phase having characteristics as described herein, in a manner in accordance with the subject methods, would provide for such a beneficial result as compared to the prior art separation protocols. As such, the claimed methods provide for unexpected results over the prior art.

Other than the impact on phase collapse, this realization by the inventors of the subject invention provides additional benefits to stationary phases. For example, advantageously, the fabrication protocols of substrates having low bonding densities of bonded phases is significantly reduced and simplified as compared to the complex fabrication protocols of substrates with higher bonding densities of bonded phases. For example, a single step reaction may advantageously be employed to fabricate substrates having low density hydrophobic phases, while multi-step reactions are required for the fabrication of substrates having high density hydrophobic bonded phases. These less complex, single step reactions reduce manufacturing cycle times and thus provide cost savings over the more complex, multi-step reactions required to fabricate hydrophobic bonded phase of higher densities, e.g., encapped phases. Still further, these simpler, single-step reactions enable increased flexibility in the selection of the particular chemistry employed in fabricating the low density hydrophobic bonded phases of the subject invention. For instance, the utilization of secondary reactions (commonly referred to as the endcapping effort) to prepare phases are not needed with the subject invention and, as such, results in reduced costs and saves time. Also, the primary reaction time may be shortened so as to utilize partial coverage when preparing a phase which would save time and effort in the preparation of material.

While hydrophobic bonded phases having low bonding densities provide most significant results in regards to phase collapse for substrates having small pore sizes (e.g., average pore size less than or equal to about 150 Å), it was realized by the inventors of the present invention that substrates having relatively larger pore sizes and higher bonding densities also benefit from the subject invention as the inventors of the subject invention have realized that, contrary to what has been previously postulated regarding bonding densities for higher pore sized substrates, in fact the amount of density of the bonded phase to a given substrate with relatively larger average pore sizes is substantially, if not completely, insignificant in regards to phase collapse. Accordingly, in light of the unexpected results realized by the inventors of the subject invention, substrates having larger pore sizes may be fabricated with low density hydrophobic bonded phases, thus decreasing manufacturing costs thereof, as described above, without substantially impacting the functionality thereof for constituent separation.

The subject methods may be employed to separate a variety of organic and inorganic constituents or analytes as will be apparent to those of skill in the art. That is, a wide variety of constituents may be separated according to the subject invention, where the subject methods may be employed to separate non-polar, polar, e.g., highly polar, and ionic constituents, sometimes in the same separation process. The constituents may be naturally occurring or synthetic, and may be pre-processed or otherwise manipulated prior to separation by the subject invention. Representative constituents include, but are not limited to, proteins, peptides, polypeptides, glycoproteins, saccharides (mono- poly- and oligo-saccharides) nucleic acids, lipids, phospholipids, fullerene compounds, glycolipids, carboxylic acids, vitamins, catecholamines, purines, pyrimidines, nucleotides, various polar pharmaceuticals, or other suitable substances that can be analyzed using a highly aqueous mobile phase. In certain embodiments, a constituent may be derivatized such that an easily detectable chemical group may be attached to the constituent, e.g., to make the constituent easy to detect once it emerges from the stationary phase. Examples of such derivatization processes include attaching an ultraviolet absorbing group to a constituent, attaching a fluorescent group to a constituent, attaching an electrochemical group to a constituent, etc.

As noted above, a feature of the subject invention is the use of a stationary phase that, when used with a highly aqueous fluid to separate constituents under suitable conditions, does not produce, or at least substantially reduces, phase collapse such that at least about 75% of retention is maintained using the subject methods, where in many embodiments at least about 85% retention is maintained and in many embodiments at least about 90% of retention or more is maintained, such that there is no excessive phase collapse.

By "stationary phase" is meant the immobile phase involved in the separation process, e.g., a chromatographic process. The stationary phases of the subject invention include a substrate (i.e., a solid support) and a bonded phase, where the bonded phase is attached, associated, connected or otherwise coupled or linked to the substrate. The immobile phase may be contrasted with the mobile phase or eluent, as will be described in greater detail below. The stationary phase employed in the subject invention may be a solid, a bonded or coated phase on a solid support, or a wall-coated phase. Typically, the stationary phase is made up of a plurality of particles, e.g., as is known in the art for HPLC protocols.

A variety of materials may be employed for the stationary phase, where suitable materials include, but are not limited to, silica (e.g., $SiO_2$), alumina (e.g., $Al_2O_3$), $TiO_2$, $ZrO_2$, and other suitable metal and metal oxides including transition metal oxides, as well as polymeric materials such as poly (styrene-divinylbenzene (PS-DVB), organo modified metals or transition metal oxides (hybrid) and continuous metal oxides or chemically modified metal oxide monolithic structures. Of interest is the use of silica, e.g., silica gel particles, for use with the subject invention, particularly spherical silica, however irregular particles may be employed as well in certain embodiments.

The inventors have realized that, contrary to what is typically thought in the art, the extent of phase collapse is directly related at least in part to the bonding density of the bonded phase associated with the substrate for a given area of the substrate, i.e., the amount, extent or magnitude of a given surface of a substrate of the stationary phase (e.g., a particle of the stationary phase) associated with a hydrophobic bonded phase. Accordingly, the inventors have discovered that there is a bonding density above which phase collapse may occur or may be increased, particularly in stationary phases having small pore sizes, e.g., average pore size below about 150 Å. Accordingly, as noted above the substrate (which may be a plurality of particles) of the stationary phase is characterized in that it has a hydrophobic phase bonded thereto, wherein the hydrophobic bonded phase is bonded to the stationary phase in a low density manner. In other words, the density of bonding of the hydrophobic bonded phase to the substrate is low. By "low bonding density" is meant that the bonding density of the hydrophobic bonded phase to the substrate of the stationary phase ranges from about 1.0 $\mu moles/m^2$ to about 3.2–3.4 $\mu moles/m^2$, e.g., from about 1.0 $\mu moles/m^2$ to about 3.0 $\mu moles/m^2$, e.g., from about 1.0 $\mu moles/m^2$ to about 2.5 $\mu moles/m^2$, for example in certain embodiments the bonding density may be about 2.0 $\mu moles/m^2$ or less such about 1.5 $\mu moles/m^2$ or less, e.g., about 1.0 $\mu moles/m^2$ or less in certain embodiments, as determined by, e.g., the method described in G. E. Beredensen and L. de Galan, J. Liq. Chromatogr., 1, 561(1978). In many embodiments, the bonding range densities provided above are average bonding densities such that a given substrate will have an average bonding density that falls within the ranges provided, i.e., the bonding density of a given substrate is an average of each unit area (m$^2$) thereof, where such average falls within the ranges provide above, but where one or more unit areas may have bonding densities that fall outside, (above or below), the described ranges.

It is to be understood that where the stationary phase is made up of a plurality of particles, the above description of bonding densities is applicable to each particle. Accordingly, the bonding density of the hydrophobic bonded phase associated with each particle is low such that the bonding density of the hydrophobic bonded phase to the stationary phase ranges from about ranges from about 1.0 μmole/m$^2$ to about 3.2–3.4 μmole/m$^2$ per particle, e.g., from about 1.0 μmole/m$^2$ to about 3.0 μmole/m$^2$ per particle, e.g., from about 1.5 μmole/m$^2$ to about 2.5 μmole/m$^2$ per particle, for example in certain embodiments the bonding density may be about 2.0 μmole/m$^2$ or less such as about 1.5 μmole/m$^2$ or less, e.g., about 1.0 μmole/m$^2$ or less in certain embodiments, as determined, e.g., using the method described above. Furthermore, in many embodiments, the bonding range densities provided above for each particle are average bonding densities such that a given stationary phase will have an average bonding density that falls within the ranges provided. For example, different particles may have different bonding densities, however the average bonding density of all the particles that make up a given stationary phase falls within the described ranges. The bonding density of a given particle may be an average of each unit area (m$^2$) of the particle, where such an average falls within the ranges provide above, but where one or more unit areas may have bonding densities that fall outside, (above or below), the described ranges.

The hydrophobic bonded phase is typically chemically bonded to the stationary phase, where methods for chemically bonding a hydrophobic phase to a substrate of a given stationary phase, e.g., for RP-HPLC, are well known to those of skill in the art. As noted above, an advantage of the subject low density bonded phases is that the protocols for bonding them to the substrates are greatly simplified over protocols required to produce bonded phases present at higher bonding densities. Such simplification reduces manufacturing cycle times and thus manufacturing costs. Typically, a majority of the hydrophobic bonded phase is positioned within the pores of the stationary phase, however a portion of the hydrophobic bonded phase may be positioned on the outside of the pores or rather the outer surface of the stationary phase, e.g., the outer surface of silica particles.

The hydrophobic bonded phase may be organic or inorganic moieties. In any event, the particular hydrophobic phase is selected to achieve optimum separation of the constituents of interest. The hydrophobic bonded phase may be any suitable bonded phase, where the choice thereof may be dictated by the particular separation protocol. Representative hydrophobic bonded phases include, but are not limited to, alkyl, phenyl, amine, and cyano bonded phases. For example cyanopropyldimethyl silane bonded phases, propyl-amino silane bonded phases, phenyl bonded phases, alkyl bonded phases, and the like may be employed with the subject invention. In many embodiments, the hydrophobic bonded phase is made up of hydrocarbon compounds which may be aliphatic (straight or branched chain) or cyclic such as phenyl compounds. Of particular interest are hydrophobic bonded phases that include hydrophobic alkyl ligands. In those embodiments where the hydrophobic bonded phase includes alkyl ligands, the alkyl ligands may be short chain alkyl ligands, e.g., as short as about two carbons, or long chain alkyl ligands, e.g., as long as about thirty carbons or more, such that the hydrophobic bonded phase of the subject invention may have alkyl ligands that have lengths that range from about 2 carbon atoms to about 30 carbon atoms, where in certain embodiments a mixture of different lengths of alkyl groups may be employed. Accordingly, in many embodiments employing silica particles, the silica is reacted with mono-, di- or tri-functional silanes containing hydrophobic groups to provide a suitable bonded hydrophobic phase. Of interest are alkyl ligands having from about eighteen carbon atoms (i.e., n-octyldecyl (C18)) to about eight carbon atoms (i.e., and n-decyl (C8)). However, in certain embodiments alkyl ligands of fewer carbon atoms (e.g., about two to about three carbon atoms or the like) or more carbon atoms may be employed. In certain embodiments employing silica particles, the silica gel is reacted with dimethylphenylchlorosilane to provide a bonded phenyl phase to the silica.

Regardless of the particular hydrophobic phase that is bonded to the stationary phase, once bonded any remaining functional groups or moieties, e.g., residual silanol groups, present on the stationary phase may be endcapped. A stationary phase is said to be "endcapped" when residual moieties or groups such as residual silanols, on a stationary phase surface, present after the bonding of the hydrophobic bonded phase (e.g., C18, C8, etc.) to the stationary phase, are further reacted with a second agent, e.g., a silyating agent, to bond or cap as many of these residual moieties (e.g., residual silanols) as possible. For example, in the case of a silica stationary phase, endcapping of residual silanols may be accomplished with a small, reactive silane such as trimethylchlorosilane or the like to produce an endcapped stationary phase. Such endcapping protocols, e.g., employing small silylating agents (e.g., trimethylchlorosilane), for performing endcapping are well known in the art and thus are not described in detail herein. However, the inventors of the subject invention have discovered that in certain embodiments endcapping contributes to phase collapse and thus in certain embodiments endcapping is not employed. For example, in many stationary phase embodiments having small pore sizes, e.g., an average pore size less than about 150 Å, and low bonding densities of the bonded phase to the substrate as described above, endcapping is not employed, further simplifying manufacturing protocols.

The bonded hydrophobic groups may or may not include one or more polar groups. In certain embodiments, the incorporation of such polar functional groups, e.g., in an alkyl ligand, close to the substrate surface of the stationary phase, e.g., the surface of a silica particle, facilitates wetting of the surface and further assists in combating phase collapse. Such embedded polar groups may include, but are not limited to, amide, urea, ether, amine, carbamate, and the like. However, it many embodiments of the subject invention, these polar groups are not employed, further simplifying the manufacturing protocol. For example, the inventors of the subject invention have found that employing a stationary phase having larger pore sizes, e.g., average pore size of about 150 Å or more, regardless of the bonding density of the bonded phase, provides unexpected results in that phase collapse was substantially reduced or all-together eliminated, i.e., at least about 75% retention is maintained, usually at least about 85% and in many embodiment 90% retention or more is maintained in such embodiments.

In accordance with the subject invention, the substrate of the stationary phase is a porous substrate. Accordingly, a wide variety of pore sizes may be employed with the subject invention, where a particular pore size is chosen to facilitate constituent separation without any, or with little, phase collapse, and allows free diffusion of the constituents to be separated into and out of the pores so that the constituents can interact with the bonded hydrophobic phase. Accordingly, in many embodiments the stationary phase may have an average pore diameter size that ranges from about 150 Å or less and in many embodiments the stationary phase may have an average diameter pore size greater than about 150 Å, as measured, e.g., using the method of Halasz (Ber. Bunsenges Phys. Chem. (1975) 79, 731) as modified by Bidlingmeyer (Anal. Chem. (1984) 56, 950) or by mercury intrusion and gas condensation/evaporation as known in the art. The average diameter pore size of a given stationary phase may range from about 60 Å to about 2000 Å, e.g., from about 80 Å to about 800 Å, e.g., from about 80 Å to about 300 Å, e.g., from about 80 Å to about 150 Å or in many embodiments ranges from about 150 Å to about 300 Å. For example, in certain embodiments the substrate includes small pore sizes (i.e., an average pore diameter size of about 150 Å or less, e.g., about 80 Å to about 150 Å) and has a low density hydrophobic bonded phase such that the bonding density of the hydrophobic bonding phase to the substrate ranges from about 1.0 μmole/m$^2$ to about 3.2–3.4 μmole/m$^2$, e.g., from about 1.0 μmole/m$^2$ to about 3.0 μmole/m$^2$, e.g., from about 1.5 μmole/m$^2$ to about 2.5 μmole/m$^2$, for example in certain embodiments the bonding density may be about 2.0 μmole/m$^2$ or less such as about 1.5 μmole/m$^2$ or less, e.g., about 1.0 μmole/m$^2$ or less in certain embodiments. Accordingly, while a given particle may have pores that vary in sizes, i.e., may have pores of different sizes, a given particle will usually have a mean or average pore diameter that falls within the ranges described above. Where the stationary phase is made up of a plurality of porous particles, each particle an average pore size that falls within the above-described ranges.

In many embodiments, all of the particles making up a given stationary phase have the same or substantially the same sized pores. However, in certain embodiments some of the particles may have pore sizes that differ from other particles such that a stationary phase may have a mix or range of pore sizes. For example, the particles of different pore sizes may be mixed together, e.g., randomly, or they may be provided in a particular form or pattern, e.g., a gradient of pore sizes may be employed. In such a pore size gradient, the mobile phase is contacted with a plurality of particles that provide a gradient of pore sizes for example from largest to smallest pore sizes or vice versa. That is, in such a gradient the pore sizes of the stationary phase contacted first are greater (or less than), i.e., are different from, the pore sizes that are contacted at a later point in time.

The total porosity of the stationary phase is chosen to optimize the particular separation procedure being performed. Accordingly, the porosity of the stationary phase of the subject invention may vary depending on the particular separation protocol being performed. In certain embodiments, total porosity of a given stationary phase or a given particle thereof, i.e., the volume that is porous/total volume of the particle, e.g., of each particle that makes up a given stationary phase, may range from about 1% to about 70%, e.g., about 1% to about 60%, as determined, e.g., by the Brunauer-Emmett-Teller (BET) method as is known in the art. Accordingly, the surface area of the stationary phase will vary depending on the particular protocol being performed, where the surface area of a stationary phase, e.g., of each particle of a given stationary phase, may range from about 600 m$^2$/gram to about 1 m$^2$/gram, usually from about 200 m$^2$/gram to about 300 m$^2$/gram and more usually about 200 m$^2$/gram In certain embodiments, the total porosity may vary within a given stationary phase. For example, a stationary phase may include a plurality of particles having various porosities such that a mixture of porosities is employed.

The size of the stationary phase is selected depending on the particular separation process. In certain embodiments, the stationary phase is relatively small and in certain other embodiments the stationary phase is relatively large. The size of the stationary phase, i.e., the size of each particle of the stationary phase in those embodiments employing a plurality of particles, may range from about 0.5 microns to about 100 microns, usually from about 0.5 microns to about 30 microns and more usually from about 1 microns to about 10 microns, where in certain embodiments particles of various sizes may be employed. When present in a chromatography column such as an HPLC column, e.g., an RP-HPLC column, the size of a given chromatography column selected for use with the subject invention may dictate the size of the stationary phase and/or the total number of stationary phase particles to be packed therein. Chromatography columns of various lengths may be used. For example, in small scale operations, columns having dimensions as small as about 10–25 microns×about 5.0 mm or smaller may be used or in large scale operations columns having dimensions as large as about 250 cm×about 3000 cm or larger may be used. Of course, columns of other sizes may be employed as well, e.g., columns having dimensions that fall above, below or between the above-described ranges.

As noted above, the subject methods include a highly aqueous fluid as the mobile phase or eluent. Typically, the highly aqueous fluid of the subject invention is selected to be more polar than the stationary phase or rather the hydrophobic bonded phase bound to the stationary phase. As the subject fluids are highly aqueous fluids, they include a significant amount of water and in certain embodiments are made entirely of water. The amount of water present in the highly aqueous fluids of the subject invention may vary depending on the particular constituents to be separated, etc. Generally, though not always, the subject highly aqueous fluids include at least about 85% water, where in many embodiments the amount of water in the highly aqueous fluids ranges from about 85% (v/v) to about 100% (v/v), e.g., 90% (v/v) to about 100%(v/v), e.g., 95% (v/v) to about 100% water. These ranges are exemplary only and are in no way intended to limit the scope of the invention as the highly aqueous fluids of the subject invention may include water in an amount less than about 85% water (v/v) in certain embodiments.

In those embodiments that include one or more additional fluids or components along with a water or aqueous component, i.e., in those embodiments where the amount of water is less than 100%, a variety of additives or solvents (i.e., modifiers) may be used or mixed with the water to provide a given highly aqueous separation fluid, where such components include buffers and various organic modifiers or solvents such as acetonitrile, methanol, propanol, ethanol, isopropanol, and the like such that a highly aqueous fluid of the subject invention may include an aqueous solvent component (i.e., water) and an organic solvent component, where the amount of aqueous component present falls within the ranges described above. Usually, the mobile phase is degassed to eliminate dissolved gas from the mobile phase fluid prior to use (and/or during use) in a separation protocol. Such degassing may be performed by heating or by vacuum (e.g., in a vacuum flask), or in-line using evacuation of a tube made from gas permeable substances such as PTFE, or by helium sparging.

In many embodiments more than one fluid may be employed in a given separation protocol (e.g., in parallel or simultaneously or in succession), where at least one of the fluids is a highly aqueous fluid as described above. For example, an isocratic elution may be employed such that the eluent, i.e., the highly aqueous fluid, is not changed during a separation run such that only one highly aqueous fluid is employed. In other embodiments, a gradient (continuous, gradual or step) elution is employed such that two or more elution compositions are employed. For example, a first fluid may be employed that is a highly aqueous fluid as described above, and at least a second fluid may also be employed, where the second fluid may or may not be a highly aqueous fluid and may be employed at the same time, before or after the first fluid and the second fluid may include the same components as the first fluid, e.g., water and acetonitrile, but in different proportions than the first fluid. In such a manner, a steady change of eluent strength is employed for a separation, e.g., one or more successive eluents may have increasing strengths such that they may include water and increasing amounts of a less polar solvent.

The water that is used to produce the subject highly aqueous fluids of the subject invention may be obtained from any convenient water source such that the water may be tap water obtained from, for example, a municipal water district. The water employed in the subject invention may be purified or otherwise treated, e.g., to remove certain undesirable agents that may be initially present therein such as certain organic and inorganic chemicals, heavy metals, etc. Such purification or treatment protocols include, but are not limited to, deionization, distillation, and the like, where such protocols are well known to those of skill in the art. The aqueous fluids of the subject invention may include a suitable buffering system, as noted above, to maintain the appropriate pH, e.g., a pH that ranges from between about 2 to about 10.

In practicing the subject methods, the highly aqueous fluid having at least two constituents is contacted with the stationary phase. Accordingly, prior to being contacted with the stationary phase, the constituents of interest, i.e., the constituents to be separated, is added to or otherwise combined with the highly aqueous fluid(s), where the constituents may be processed prior to such combining. The constituents may be included in a sample, where the term "sample" as used herein relates to a material or mixture of materials, typically, although not necessarily, in fluid form, containing one or more constituents of interest. A sample may be any suitable sample that includes at least two constituents, where the sample and/or the constituents may be pre-processed prior to separation, e.g., may be amplified, denatured, fractionated, etc. Representative samples may include, but are not limited to, biological fluids such as blood, serum, urine, tears, etc., as well as non-biological fluids such as water, buffer and the like.

Once the constituents of interest are combined with the highly aqueous fluid, the constituent-containing highly aqueous fluid is contacted with the stationary phase under conditions sufficient to separate at least two constituents of the highly aqueous fluid. In this manner, the constituents are retained for a period of time by the hydrophobic phase present in the pores of the stationary phase to separate them. As described above, the subject invention allows the hydrophobic bonded phase, e.g., the alkyl bonded phase, to remain substantially, and in many embodiments fully, accessible when contacted with the highly aqueous mobile phase, thereby preventing or substantially reducing phase collapse, where the bonded phase such as an alkyl chain or the like collapses or mats down as described above.

Accordingly, because the stationary phase is hydrophobic or less polar than the mobile phase, the elution order of sample constituents is generally related to their hydrophobic properties. The more hydrophilic the solute, the faster it will be eluted (i.e., the less is will be retained by the stationary phase) while the more hydrophobic it is, the slower it will be eluted (the more it will be retained by the stationary phase). In those embodiments that employ a mobile phase gradient that increase in concentration of an organic modifier (usually acetonitrile or methanol) as described above elute constituent molecules in order of increasing hydrophobicity.

Typically, the constituent-containing highly aqueous fluid is flowed over or through the stationary phase at a flow rate that is suitable for the particular constituent separation, where the flow rate may range from about 0.001 μL/min to about 10,000 μL/min, usually from about 1 μL/min to about 10,000 μL/min and more usually from about 100 μL/min to about 5000 μL/min and the pressure under which the mobile phase is contacted with the stationary phase ranges from about 10 psi to about 60,000 psi or more, usually from about 100 psi to about 10,000 psi and more usually from about 1000 psi to about 6000 psi. The subject separation protocol is usually contacted with the stationary phase at temperatures that range from about 4° C. to about 95° C. and usually from about 25° C. to about 50° C.

The amount or volume (i.e., the elution volume or $V_R$) of the mobile phase required to elute a constituent from the stationary phase will vary depending on the particulars of the mobile phase, stationary phase and constituents to be eluted. Typically, the elution volume ranges from about 20 microliters to about 7,500 ml, usually from about 0.2 ml to about 60 ml and more usually from about 0.2 ml to about 30 ml.

Once eluted, the eluate or effluent (i.e., the combination of the mobile phase and constituents exiting the stationary phase) is detected by a suitable detector, where a variety of detectors are known for such detection. Such detectors include ultraviolet (UV-VIS) detectors wherein the eluate is irradiated with a light source and the amount of light that passes from the light source, through the eluate and to the detector, is measured. Refractive index reflectors may also be employed wherein the detector measures the deflection of light by the eluate, where each constituent has a unique refraction index. Electrochemical detectors may also be employed in certain embodiments, wherein an electrochemical detector responds to analytes that can be oxidized or reduced at an electrode over which the eluate passes. In this manner, electric current through the electrode increases in proportion to the amount of constituent in the eluate. Also of interest are fluorescent detectors which respond to constituents in the eluate that fluoresce. In using such a fluorescent detector, the eluate is irradiated and the emission wavelengths are measured wherein the emission intensities are proportional to the amount of constituent in the eluate. Mass spectrometers may also be employed to detect and analyze separated constituents. Accordingly, the presence of constituents in the eluate may be recorded by mass spectroscopy, by detecting a change in UV-VIS absorption at a set wavelength, by refractive index, by fluorescence after excitation with a suitable wavelength, by electrochemical response, and the like. Regardless of the type of detector employed, typically the detector is coupled to a user interface or readout for communicating the results of the detection to a user.

Certain embodiments may include obtaining data related to the above-described constituent separation methods, for example data related to a process parameter, results relating to the detection of one or more constituents, etc., and further processing or manipulating the data and/or forwarding, e.g., by communication, or transmitting the data. Such results may be raw results or may be processed results such as obtained by comparing a result or data point to a predetermined reference or standard and forming conclusions based on this comparison such as whether or not a particular constituent is present in the sample and/or the amount thereof The results of the reading (processed or not) may be forwarded (such as by communication) to a remote location if desired, and received there for further use (such as further processing), as now described in greater detail.

In certain embodiments, data relating to the subject methods, may be transmitted to a remote location. By "remote location" it is meant a location other than the location at which the separation protocol and/or constituent detection occurs. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient electronic or telecommunications means may be employed for transmitting the data, e.g., facsimile, modem, Internet, etc.

Systems

Also provided are systems for separating at least two constituents of a highly aqueous fluid. As noted above, in certain embodiments the subject methods are methods of performing LC, e.g., HPLC, e.g., RP-HPLC. As such, in accordance with the subject invention, systems for use in practicing the subject methods using a chromatography protocol such as a HPLC protocol are provided. In general, the subject systems include a stationary phase having a low density hydrophobic bonded phase, a highly aqueous fluid having at least two constituents and an apparatus configured to perform an LC protocol such as an HPLC or RP-HPLC protocol. The systems of the subject invention typically also include a fluid delivery system, a sample injection system, e.g., a sample injection valve, a separation column, and a detector, where some or part of the system may be automated.

FIG. 1 shows an exemplary embodiment of a system 10 according to the subject invention, where the system is configure to be utilized in an HPLC protocol, e.g., a RP-HPLC protocol. As shown in FIG. 1, system 10 includes a variety of components, where some of the components may be optional (e.g., a guard column, additional reservoirs, etc.).

As shown, system 10 includes at least one fluid reservoir 12 for containing a highly aqueous fluid, i.e., a mobile phase, as described above. In certain embodiments, only one reservoir is provided that includes the mobile phase to be used, e.g., 100% water or water mixed with at least one additional organic additive or modifier, such as methanol or the like, in a suitable proportion to the water. In certain embodiments, additional reservoirs are provided such as optional reservoir 13, where such may include a different mobile phase, e.g., a second mobile phase, or different proportions of a mobile phase, or may include an additive or modifier to be added to the aqueous component contained in reservoir 12. In this manner, the proportion of the components of the mobile phase may be altered, e.g., gradually or step-wise, during a given protocol by adjusting the amount of fluid allowed to flow from a given reservoir. For example, a first reservoir such as reservoir 12 may contain 100% water and a second reservoir may contain an organic modifier such as methanol or acetonitrile or the like. In use, the fluids contained in the reservoirs may be combined in a particular proportion to be used throughout the entire separation process or may be combined in various proportions, where the proportion may vary at different times throughout the separation process such that a first fluid may be 100% water, where such may be followed by various fluids of decreasing proportions of water and increasing proportions of the organic modifier, such as 95% water and 5% organic solvent, 90% water and 10% organic solvent, etc. The constituents of interest, i.e. to be separated, may be added to the reservoirs, but are typically combined with the mobile phase at a later location (see sample introduction syringe or valve 24). Regardless of the number of reservoirs employed, typically each is coupled to an outgassing element 8 and 9 for degassing the fluid contained in the reservoir. An optional mixing vessel 15 may be included when two or more reservoirs are employed to ensure complete mixing of the components of the mobile phase.

Fluid from the reservoir(s) are typically passed through a suitable filter element 14 (and optional additional filter 7) to eliminate or substantially reduce any contaminants or elements that may be deleterious to the column or the constituents of interest. Fluid is then pumped, via pump 16, through a pressure relief and vent 18 and a pressure gauge 20 is typically employed at a suitable location in-line, usually prior to fluid entering the separation column 28 and may also be prior to entering optional guard column 22. Pump 16 may be any suitable pump such as a reciprocating piston pumps, a syringe type pump, a constant pressure pump, etc. Usually, pump 16 provides a steady high pressure with no pulsations and may be programmed to vary the composition of the mobile phase during the course of the separation.

In many embodiments, a small "guard" column 22 may be positioned before or after the sample injection port 26, but before the analytical or separation column 28. This optional guard column 22 protects the separation column 28 against components in the mobile phase that may be harmful to the system and/or the separation process such as components that may clog the separation column 26, compounds and ions that may cause "baseline drift", decreased resolution, decreased sensitivity, and create false peaks; compounds that may cause precipitation upon contact with the stationary or mobile phase, and compounds that might co-elute and cause extraneous peaks and interfere with detection and/or quantification. Guard column 22 may be packed with the same stationary phase as separation column 28 and may be of the same inner diameter as column 28, but may be packed with a different stationary phase than separation column 28 and/or have different dimensions, e.g., a shorter length.

A temperature-regulating element 23 for use in regulating the temperature of the separation process may be coupled with the system, herein shown positioned prior to sample introduction element 26, but may be positioned in any convenient location.

Samples are typically injected into the system via an injection port 26. The injection port of an HPLC system usually includes an injection valve and a sample loop (not shown). The sample is drawn into a syringe 24 and injected into the loop via the injection valve. A rotation of the valve rotor closes the valve and opens the loop in order to inject the sample into the stream of the mobile phase. Loop volumes may range between about 1 µl to about 100 ml or more, where in many embodiments the loop volumes may be less than about 1 µl or more than about 100 ml. As noted above, in certain embodiments a sample may be added to the mobile phase at an earlier location in the system, e.g., to one or more reservoirs. In many systems, sample injection may be automated.

As shown, separation column 28 includes the stationary phase 27 of the subject invention. Separation column 28 may be fabricated from any suitable material such as glass, stainless steel or plastic. The dimensions of column 28 may vary depending on a variety of factors relating to a particular separation process, e.g., the constituents of interest, the stationary phase, the mobile phase, etc. For example, a column may have a length that ranges from about 5 mm to about 3000 cm, usually from about 10 mm to about 300 mm and more usually from about 50 mm to about 300 mm, and an internal diameter or width that ranges from about 0.01 mm to about 250 cm or more, usually from about 0.1 mm to about 8 mm and more usually from about 0.1 mm to about 4.6 mm Of course, columns having dimensions other than those described above may also be employed. In many embodiments, the total volume of mobile phase in a given column or void volume or interstitial volume (the remainder of the column is taken up by the stationary phase) may range from about 1% to about 70% of the total volume of an empty column, wherein certain embodiments it maybe about 50% of the total volume of an empty column. The separation column usually, though not necessarily, includes end fittings (not shown) at one or both ends of the column that connects the column to the sample injector and/or detector. Oftentimes such endfittings include a frit to hold or contain the stationary phase in a suitable packing configuration (e.g., a dense packing configuration), where such frits may be made from any suitable porous material such as stainless steel or other inert metal or plastic such as PTFE or polypropylene.

System 10 also includes a suitable detector 29 for detecting constituents of the eluant as the eluant exits column 28. As noted above, suitable detectors include mass spectrometers, UV-VIS detectors, refractive index detectors, fluorescent detectors, electrochemical detectors, etc. In many embodiments detector 29 is operatively associated with an amplifier 30 for amplifying the signal produced by the detector and also to a user interface or readout 32 for communicating or displaying the results of the detector to a user. The system may be operatively coupled to a data collection unit such as a computer 34 which may be integrated with one or more components of the system, i.e., a unitary piece of construction, or may be a separate component.

Kits

Finally, kits for use in practicing the subject methods are provided. The subject kits include at least a stationary phase having a low density hydrophobic bonded phase and instructions for using the stationary phase in the practice of the subject methods. The stationary phase included with the subject kits may be provided in a column or tube, e.g., for performing LC or HPLC or RP-HPLC, such that a given kit may include a column packed with the stationary phase of the subject invention. The instructions that are provided with the subject kits are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions may be recorded on a suitable substrate.

The subject kits may also include at least some, if not all, of the components for preparing a highly aqueous fluid described above. As such, the kits may include one or more containers such as vials or bottles, with each container containing a separate component of a highly aqueous fluid. For example, a kit may include a prepared highly aqueous fluid, e.g., water and a modifier, or may include one or more components to prepare such a fluid such as one or more of: HPLC grade water, HPLC grade modifier, such as methanol, acetonitrile, propanol, ethanol, isopropanol, etc.

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All columns were tested with an Agilent Technologies 110 HPLC equipped with solvent degasser, binary pump, heated column compartment set to 25° C., an autosampler set to inject 5 µL and a diode array detector set at 254 nm. All columns were 4.6 mm i.d.×150 mm long. The stationary phases included 5 micron silica particles with bonded hydrocarbon groups. The stationary phases differed in various properties as described below.

Two mobile phases were prepared. A first mobile phase was a highly organic mobile phase (mobile phase A) made of 75% pesticide grade methanol (from Burdick and Jackson) and 25% in HPLC grade deionized water. A second mobile phase was a highly aqueous phase made of 50 mM sodium acetate (from J. T. Baker) in HPLC grade deionized water at pH 4.6 (100% buffered water). The flow rate of each mobile phase was set at 2 ml/min.

The test samples used in the experiments were a series of water-soluble B vitamins from Aldrich Chemical Co. 0.25 mg/ml of each of: Nicotinic Acid, Pyridoxine, Thiamin and Niacinamide were dissolved in mobile phase B. For the analyses, 1 μL of this mobile phase B/vitamin mixture was injected into a column.

The following procedure was used for each test. Mobile phase A was pumped through each column for 20 minutes to insure the column was fully equilibrated. Mobile phase B was then pumped for 20 minutes followed by a measurement of k' (capacity factor) for duplicate injections of a given test sample. After analysis was complete, the flow was turned off for 10 minutes. Flow was then turned back on for 2 minutes, followed by measurement of k' for duplicate injections of a given test sample. The capacity factors (k') calculated before and after flow of mobile phase was turned off were compared. The percent difference between the two capacity factors (i.e., (k' in mobile phase B after flow was stopped/k' in mobile phase B before flow was turned off)×100) represents a measure of the magnitude of the phase collapse for a given column.

The following stationary phases were tested (relevant physical properties of the bonded phase are also provides such as silica pore size, surface area and surface coverage (bonding density):

| Phase | Pore Size | Surface Area | Surface Coverage |
|---|---|---|---|
| A1 C18 | 80 Å | 180 $m^2/g$ | 2.0 $\mu mole/m^2$ |
| A2 C18 | 100 Å | 200 $m^2/g$ | 2.0 $\mu mole/m^2$ |
| A3 C18 | 150 Å | 120 $m^2/g$ | 2.0 $\mu mole/m^2$ |
| A4 C18 | 300 Å | 50 $m^2/g$ | 2.0 $\mu mole/m^2$ |
| B1 C18 | 80 Å | 180 $m^2/g$ | 3.4 $\mu mole/m^2$ |
| B2 C18 | 150 Å | 120 $m^2/g$ | 3.4 $\mu mole/m^2$ |
| B3 C18 | 300 Å | 50 $m^2/g$ | 3.4 $\mu mole/m^2$ |
| B4 C18 | 800 Å | 16 $m^2/g$ | 3.4 $\mu mole/m^2$ |
| C1 C18 | 80 Å | 180 $m^2/g$ | 3.3 $\mu mole/m^2$ |
| C2 C18 | 300 Å | 50 $m^2/g$ | 3.3 $\mu mole/m^2$ |
| C3 C18 | 800 Å | 15 $m^2/g$ | 3.3 $\mu mole/m^2$ |
| D1 C8 | 80 Å | 180 $m^2/g$ | 2.0 $\mu mole/m^2$ |
| D2 C8 | 300 Å | 50 $m^2/g$ | 2.0 $\mu mole/m^2$ |
| E CN | 80 Å | 180 $m^2/g$ | 2.0 $\mu mole/m^2$ |
| F Phenyl | 80 Å | 180 $m^2/g$ | 2.0 $\mu mole/m^2$ |
| G $NH_2$ | 70 Å | 300 $m^2/g$ | 3.0 $\mu mole/m^2$ |

The results are shown in FIG. 2. In general, the inventors of the present invention have unexpectedly discovered one or more factors including, but not limited to, bonding density, pore size, surface hydration, alkyl bonded length, that are responsible for or contribute to phase collapse and thus such factor(s) may be optimized or manipulated to minimize or eliminate phase collapse, where the particular factor(s) and optimization may be dependant upon the particular stationary phase chemistry.

As shown, increasing bonding density does not contribute significantly to the prevention of phase collapse. As noted above, up until this discovery by the present inventors, it was thought that high bonding density was important in decreasing phase collapse. In fact, the inventors of the present invention have found the unexpected results that the opposite is true; namely, increased bonding density increases the likelihood of phase collapse—as shown by the data provided herein. For example, comparisons of stationary phases A1, B1 and C1; A3 and B2; and A4, B3 and C2, show an increase in the magnitude of phase collapse with increasing bonding density if the pore size remains the same. Accordingly, the inventors have found that a low bonding density is an important factor in the minimization or prevention of phase collapse.

Furthermore, the inventors of the present invention have also found that the hydration of the silica surface is also an important factor in limiting phase collapse—as shown by the data provided herein. For example, the A, D, E and F phases are not endcapped. Therefore, silica surface silanols are available for hydration by the aqueous mobile phase. The hydrated silica surface helps to minimize or prevent the collapse of the hydrocarbon stationary phase.

Conversely, the B and C phases are highly endcapped. There are few surface silanol groups available for hydration. The magnitude of phase collapse is increased relative to non-endcapped stationary phases.

Furthermore, the inventors of the present invention have realized another unexpected result in regards to phase collapse, as shown by the data provided herein. Specifically, increasing pore size decreases the magnitude of phase collapse. Unfortunately, increasing pore size decreases surface area leading to decreased analyte retention, as can be observed from the data provided herein. However, the inventors of the present invention have found the unexpected result that there is an optimum pore size where phase collapse is limited but where there is sufficiency analyte retention. The inventors have discovered that there is an optimum average pore size that is unique for each phase chemistry depending on the phase bonded to silica as well as if the phase is endcapped or not, whereby phase collapse is minimized or prevented—as shown by the data provided herein.

Still further, the inventors of the present invention have realized another unexpected result in regards to phase collapse; namely that reducing the alkyl chain length reduces the optimum pore size needed to prevent phase collapse, as shown by the data provided herein. For example, stationary phases like D C8 and F Phenyl do not show significant phase collapse even with an average pore sizes of 80 Å. Conversely, increasing the alkyl chain length increases the optimum pore size needed to prevent phase collapse. The C C18 phase has a unique bidentate structure with two C18 groups not directly bound to the silica surface thus increasing the stationary phase chain length. Increasing the effective alkyl chain increased the level of phase collapse relative to the other C18 phases tested even though the bonding density was less than the B C18. The inventors of the present invention have realized, unexpectedly, that using short alkyl chain lengths in combination with incorporation of polar groups like CN and amine have the added benefit of increased hydration by the aqueous mobile phase which minimizes or prevents phase collapse.

It is evident from the above results and discussion that the above described invention provides important new methods and devices for separating constituents of a highly aqueous fluid. Specifically, the subject invention provides methods and devices for separating constituents of a highly aqueous fluid that are substantially resistant, and in many embodiments, completely resistant, to phase collapse, are easy to use and are cost effective. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A system for separating at least two constituents of a highly aqueous fluid, said system comprising:
   (a) a stationary phase having a low density hydrophobic bonded phase and a pore size that ranges from about 80 Å to about 1000 Å wherein said low density ranges from about 1.0 μmole/m$^2$ to about 3.2 μm/m$^2$;
   (b) a highly aqueous fluid comprising at least two constituents; and
   (c) an apparatus configured to perform liquid chromatography.

2. The system of claim 1, wherein said stationary phase is present in a high performance liquid chromatography column.

3. The system of claim 1, wherein said highly aqueous fluid comprises from about 85% to about 100% water.

4. The system of claim 1, wherein said low density ranges from about 1.0 μmole/m$^2$ to about 3.0 μm/m$^2$.

5. The system of claim 4, wherein said low density is about 2.0 μmole/m$^2$ or less.

6. The system of claim 1, wherein said stationary phase comprises a plurality of particles and each of said particles comprises a low density hydrophobic bonded phase and a pore size that ranges from about 80 Å to about 1000 Å.

7. The system of claim 1, wherein said low density ranges from about 1.0 μmole/m$^2$ to about 3.0 μm/m$^2$ per particle.

8. The system of claim 7, wherein said low density is about 2.0 μmole/m$^2$ or less per particle.

9. The system of claim 1, wherein said hydrophobic bonded phase is chosen from alkyl, phenyl, amine, and cyano bonded phases.

10. The system of claim 9, wherein said hydrophobic bonded phase comprises alkyl ligands.

11. The system of claim 10, wherein each of said alkyl ligands comprises from about 8 carbon atoms to about 18 carbon atoms.

12. The system of claim 1, wherein said stationary phase comprises a plurality of particles, wherein each of said particles has a total porosity that ranges from about 1% to about 70%.

13. The system of claim 1, wherein said stationary phase comprises a plurality of particles, wherein each of said particles has a size that ranges from about 0.5 microns to about 100 microns.

14. The system of claim 1, wherein said stationary phase comprises a material chosen from silica, metals, metal oxides, modified metal oxides and polymers.

15. The system of claim 14, wherein said material is silica.

16. The system of claim 1, wherein said hydrophobic bonded phase does not comprise polar groups.

17. The system of claim 1, wherein said hydrophobic bonded phase comprises polar groups.

18. The system of claim 1, wherein said stationary phase is endcapped.

19. The system of claim 1, wherein said stationary phase is not endcapped.

20. The system of claim 1, further comprising a detector for detecting at least one of said at least two constituents following separation of said at least two constituents.

21. The system of claim 20, further comprising a means for communicating data representing a result of said detector to a user.

22. The system according to claim 20, further comprising a means for transmitting data representing a result of said detector to a remote location.

* * * * *